US012446883B2

(12) United States Patent
Fortson

(10) Patent No.: US 12,446,883 B2
(45) Date of Patent: Oct. 21, 2025

(54) COMPRESSION DEVICE FOR CLOSING TISSUE OPENINGS AND METHODS OF USING THEREOF

(71) Applicant: Abbott Cardiovascular Systems, Inc., Santa Clara, CA (US)

(72) Inventor: Aaron M. Fortson, Fremont, CA (US)

(73) Assignee: Abbott Cardiovascular Systems, Inc., Santa Clara, CA (US)

(*) Notice: Subject to any disclaimer, the term of this patent is extended or adjusted under 35 U.S.C. 154(b) by 169 days.

(21) Appl. No.: 17/517,989

(22) Filed: Nov. 3, 2021

(65) Prior Publication Data

US 2022/0142646 A1 May 12, 2022

Related U.S. Application Data

(60) Provisional application No. 63/110,574, filed on Nov. 6, 2020.

(51) Int. Cl.

*A61B 17/12* (2006.01)
*A61B 17/08* (2006.01)
*A61F 13/00* (2024.01)

(52) U.S. Cl.

CPC ........ *A61B 17/12* (2013.01); *A61B 2017/086* (2013.01); *A61B 2017/12004* (2013.01); *A61F 2013/0028* (2013.01)

(58) Field of Classification Search

CPC . A61B 17/085; A61B 2017/086; A61B 17/12; A61B 2017/12004; A61B 17/0466; A61B 2017/081; A61B 17/08; A61B 2017/088; A61B 17/083; A61B 2017/00951; A61F 2013/0028

See application file for complete search history.

(56) References Cited

U.S. PATENT DOCUMENTS

| | | | | |
|---|---|---|---|---|
| 3,971,384 A * | 7/1976 | Hasson | A61B 17/085 606/218 |
| 4,222,383 A * | 9/1980 | Schossow | A61B 46/00 128/853 |
| 4,881,546 A * | 11/1989 | Kaessmann | A61B 17/085 606/217 |
| 8,721,629 B2 | 5/2014 | Hardman et al. | |
| 10,010,710 B2 | 7/2018 | Belson et al. | |
| 10,426,474 B2 | 10/2019 | Christiansen et al. | |
| 10,456,136 B2 | 10/2019 | Belson et al. | |
| 2004/0193216 A1* | 9/2004 | Deutsch | A61B 17/085 606/213 |

(Continued)

FOREIGN PATENT DOCUMENTS

CN 104665886 A * 6/2015

OTHER PUBLICATIONS

CN 104665886 translated description. (Year: 2015).*

*Primary Examiner* — Diane D Yabut

(74) *Attorney, Agent, or Firm* — Workman Nydegger

(57) ABSTRACT

A compression device for compressing an area of tissue surrounding a tissue opening to close the tissue opening. The device includes a compression support frame having an outer peripheral edge forming an arc whose central angle is less than 180° and greater than 45°. The device also includes a compression support and a tension member. The compression support is mounted on the compression support frame, and the tension member is selectively slidable in relation to the compression support.

16 Claims, 15 Drawing Sheets

(56) References Cited

U.S. PATENT DOCUMENTS

| | | | | |
|---|---|---|---|---|
| 2008/0228219 | A1* | 9/2008 | Weiser | A61B 17/085 606/215 |
| 2010/0197999 | A1* | 8/2010 | Deegan | A61F 2/0045 600/30 |
| 2015/0105822 | A1* | 4/2015 | Belson | A61B 17/085 606/217 |
| 2017/0240327 | A1* | 8/2017 | Sanders | B65D 63/18 |
| 2019/0290278 | A1* | 9/2019 | Xu | A61B 17/085 |
| 2020/0205833 | A1* | 7/2020 | Christiansen | A61B 17/085 |
| 2020/0323696 | A1* | 10/2020 | Lebner | A61F 13/0259 |
| 2021/0128151 | A1* | 5/2021 | Jacobs | A61B 17/08 |
| 2021/0196275 | A1* | 7/2021 | Belson | A61B 17/085 |
| 2021/0212685 | A1* | 7/2021 | Lamps | A61B 17/0281 |
| 2021/0219973 | A1* | 7/2021 | Zhang | A61B 17/0466 |

* cited by examiner

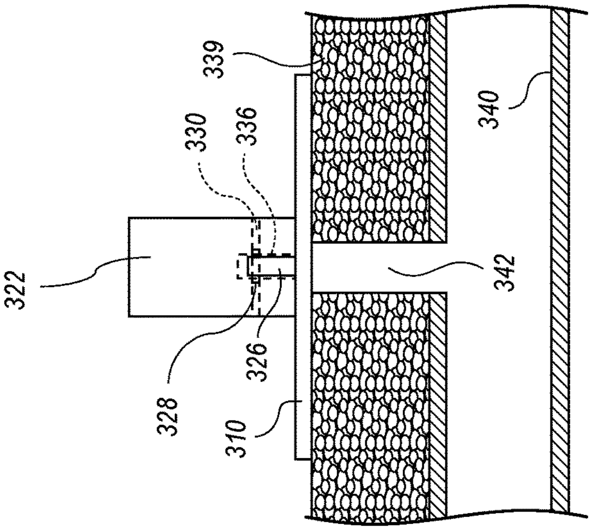
FIG. 3C
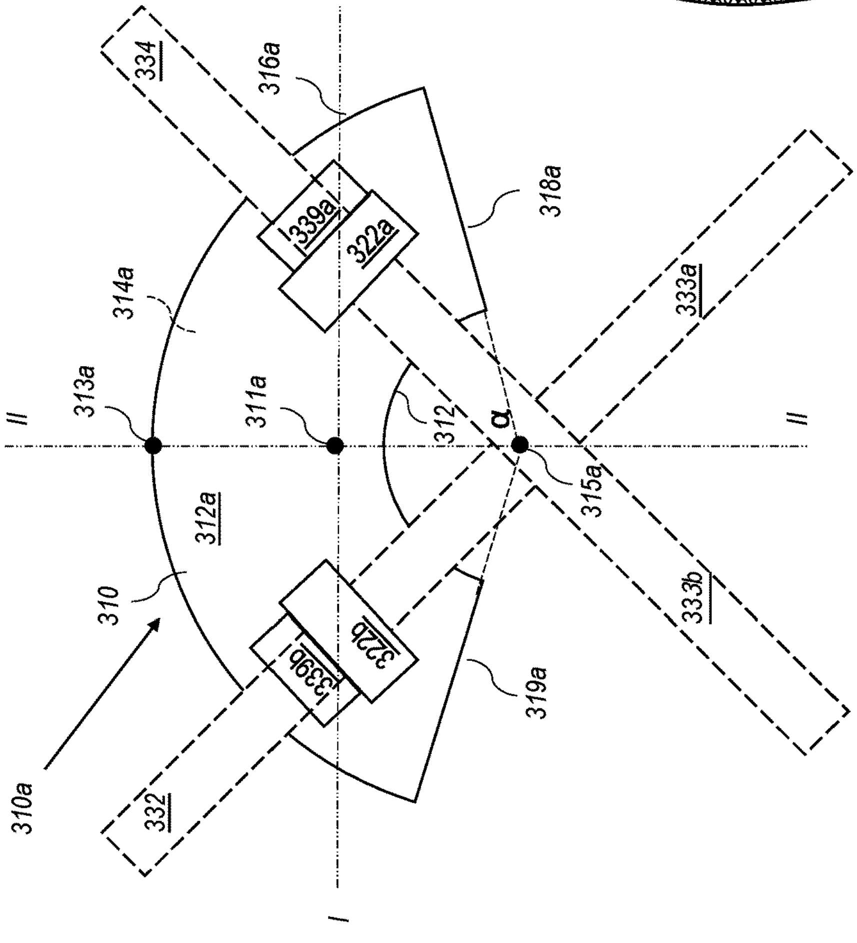
FIG. 3B
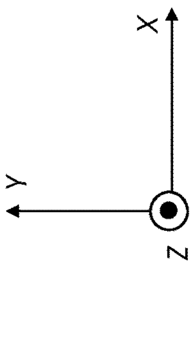

COMPRESSION DEVICE FOR CLOSING TISSUE OPENINGS AND METHODS OF USING THEREOF

CROSS-REFERENCE TO RELATED APPLICATIONS

This application claims benefit and priority to U.S. Provisional Patent Application No. 63/110,574, filed Nov. 6, 2020, the entire contents of which are incorporated by reference herein.

BACKGROUND

1. The Field of the Invention

The present invention is a tissue closure device. More specifically, the present invention relates generally to a tissue closure device that can reduce the need for hospital staff to apply manual compression to a tissue opening, such as an access site associated with a vascular procedure.

2. Background and Relevant Art

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique. Vascular access is generally provided through an introducer sheath, which is positioned to extend from outside the patient body into the vascular lumen. When vascular access is no longer required, the introducer sheath is removed and bleeding at the puncture site stopped.

One common approach for providing hemostasis (the cessation of bleeding) is to apply external force near and upstream from the puncture site, typically by manual compression. This approach suffers from a number of disadvantages. For example, the manual compression procedure is time consuming, frequently requiring one-half hour or more of compression before hemostasis is achieved. Additionally, such compression techniques rely on clot formation, which can be delayed until anticoagulants used in vascular therapy procedures (such as for heart attacks, stent deployment, non-optical PTCA results, and the like) wear off. The anticoagulants may take two to four hours to wear off, thereby increasing the time required before completion of the manual compression procedure.

Further, the manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time, renewed bleeding may occur, resulting in blood loss through the tract, hematoma and/or pseudo-aneurysm formation, as well as arteriovenous fistula formation. These complications may require blood transfusion and/or surgical intervention.

The incidence of complications from the manual compression procedure increases when the size of the introducer sheath grows larger, and/or when the patient is anticoagulated. The compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

To overcome the problems associated with manual compression, the use of bioabsorbable sealing bodies is one example approach that has been proposed. Generally, this example approach relies on the placement of a thrombogenic and bioabsorbable material, such as collagen, at the superficial arterial wall over the puncture site. While potentially effective, this approach suffers from a number of problems. For example, bioabsorbable sealing bodies may lack a solid mechanical attachment of the sealing body to the tissue. Due to the lack of a solid mechanical attachment, the sealing body can wander within the tissue tract or move out of the puncture site, thus causing late bleeds. Conversely, if the sealing body wanders and intrudes too far into the arterial lumen, due to the lack of a solid mechanical attachment, intravascular clots and/or collagen pieces with thrombus attached can form and embolize downstream, causing vascular occlusion.

In addition to not having a solid mechanical attachment to the tissue, the sealing bodies may rely upon expandable materials to achieve hemostasis. Again, the expandable materials lack the security of a hard mechanical closure, thus potentially causing late bleeds and prolonging hemostasis.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Embodiments of the present invention provide systems, methods, and devices for closing an opening in tissue.

The present disclosure describes methods and devices that may be employed for compressing tissue surrounding a tissue opening for closing the tissue opening and/or providing hemostasis. For example, according to an embodiment, a compression device may include a compression support frame, one or more compression support(s) mounted to the compression support frame, and one or more tension member selectively slidable in relation to the compression support. In some embodiments, the compression support frame has an outer peripheral edge forming an arc whose central angle is less than 180° and greater than 45°.

According to another embodiment, the compression support is rotatably mounted to the compression support frame. The compression support frame includes a body having an adhesive configured to be adhered on a tissue contact side of the body.

Another embodiment according to the present disclosure is directed to a method for using the compression device for closing a tissue opening and/or providing hemostasis. The method includes applying one or more compression support frames on an area of tissue surrounding a tissue opening. The method also includes compressing the area of tissue by adjusting the one or more tension members. The application of the one or more compression support frames is performed prior to vascular access, and compressing the tissue area is performed after the vascular access. As such, the tissue area can be readily compressed soon after the vascular access. According to another embodiments, the compression device may be used in conjunct with Hemostatic patches or standard gauze patches Additional features and advantages of exemplary implementations of the invention will be set forth in the description which follows, and in part will be obvious from the description, or may be learned by the practice of such exemplary implementations. The features and advantages of such implementations may be realized and obtained by means of the instruments and combinations particularly pointed out in the appended claims. These and other features will become more fully apparent from the following description and appended claims or may be learned by the practice of such exemplary implementations as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 3A-3C illustrate various portions of the compression device of FIG. 2.

DETAILED DESCRIPTION

Figure 1A:
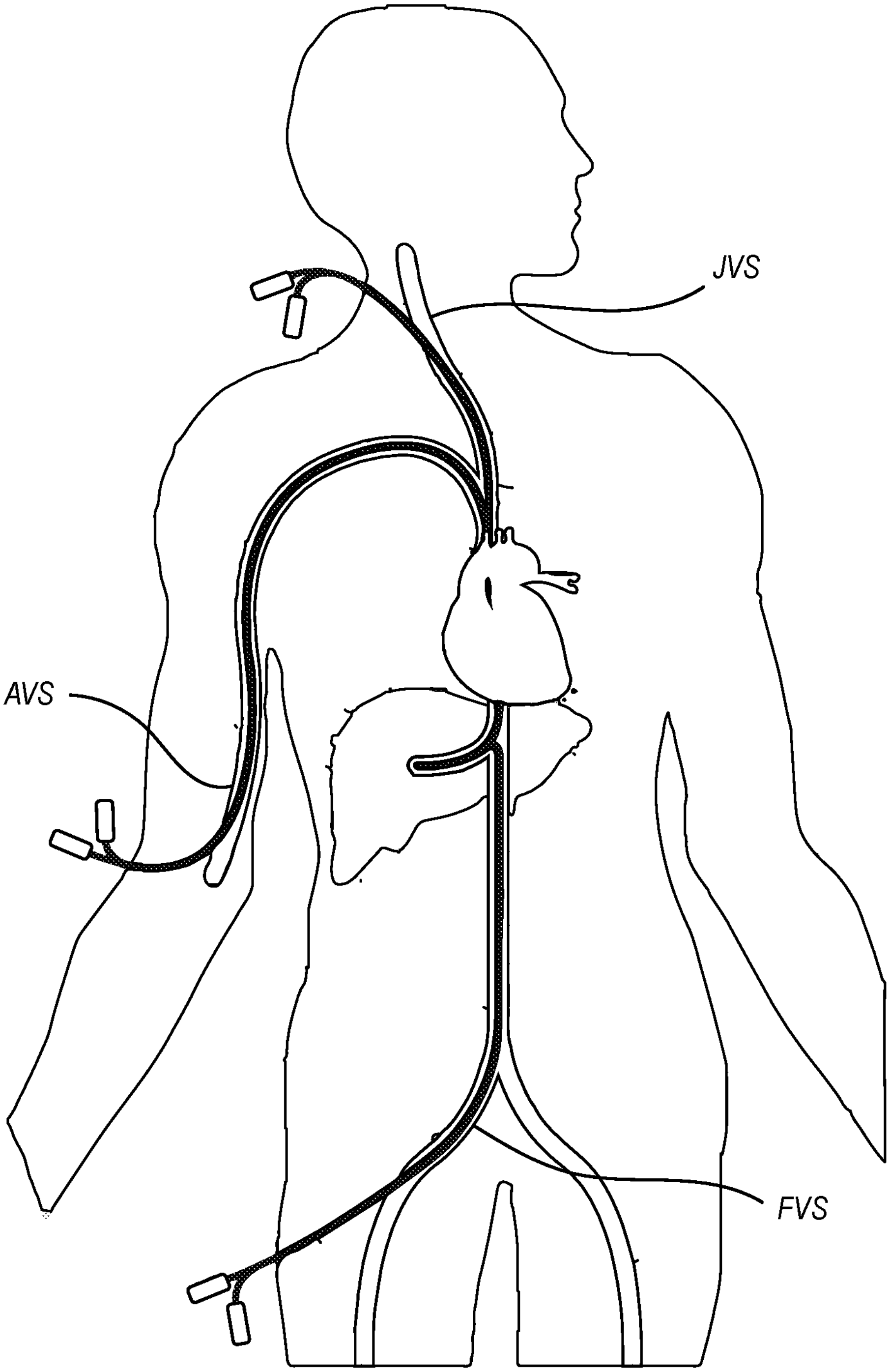
FIGS. 1A-1C illustrate common vascular access sites for a patient.

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to devices and methods for closing a tissue opening and/or providing hemostasis. The compression devices and method may be used to compress tissue near the vascular access site for closing the tissue opening caused by the vascular access. As used here, like reference numerals will be used for like structures and the discussions or disclosure of one feature is also applicable to other like features and structures.

While the present disclosure will describe a particular implementation of the compression devices and methods, it should be understood that the compression devices and method described herein may be applicable to uses, including and not limited to compressing tissue areas for other purposes and/or closing tissue openings caused by other means. Additionally, elements described in relation to any embodiment depicted and/or described herein may be combinable with elements described in relation to any other embodiment depicted and/or described herein.

I. Introduction

A. Vascular Access

Figure 1B:
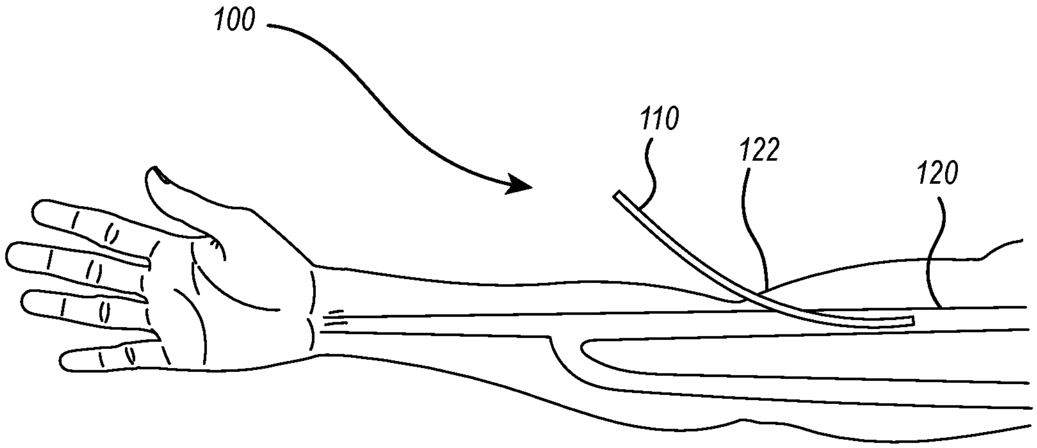
Figure 1C:
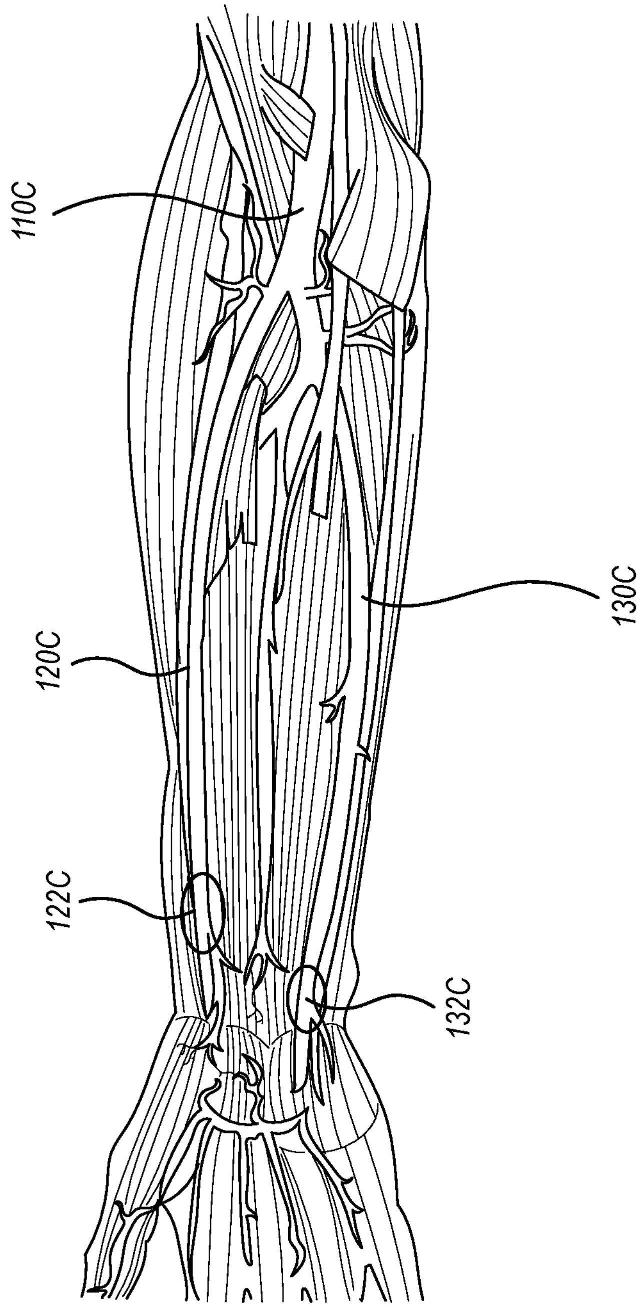

Vascular access is one of the most basic yet critical components of patient care both in hospitals and in ambulatory patient settings. Safe and reliable vascular access is an important issue in daily practice. Access is most commonly achieved via the Seldinger technique. FIG. 1A illustrates various common vascular access sites for a patient, including (but not limited to) an antecubital vascular site (AVS), a jugular vascular site (JVS), and a femoral vascular site (FVS). FIG. 1B further illustrates an enlarged view of an antecubital vascular access site 100, where a catheter 110 is inserted into a lumen of a vessel 120 via a puncture or opening 122 extending from the surface of the skin through the tissue layer(s) to the vessel. A vascular access site may be a venous access site or an artery access site. FIG. 1C further illustrates ulnar artery 130C and radial artery 120C (which are two branches of the brachial artery 110C) in a forearm and palmar blood flow having an ulnar artery puncture/access site 132C and a radial puncture/access site 122C.

The most common form of vascular access is a peripheral venous cannula which is generally inserted into veins of the hands, forearms, and occasionally feet. A catheter is introduced to the vascular system at a convenient access location and guided through the vascular system to a target location using established techniques. In some situations, vascular access is obtained by inserting catheters into the large central vessels of the body, such as the internal jugular, subclavian, or femoral vessels. This type of vascular access may be done with central venous catheters (CVCs), and is required in certain situations where peripheral access is inadequate. Such situations include, but are not limited to, the need for long-term vascular access, administering of medications that can damage smaller veins (e.g., chemotherapy), measuring central venous pressure, or obtaining certain blood tests (e.g., central venous oxygen saturation). Midline access is a type of peripheral vascular access inserted into peripheral veins that extends farther than standard peripheral catheters but does not yet reach the large central veins of the thorax. They are used when intermediate-term access is needed or when administering medications that are highly irritating to smaller veins.

II. Device for Closing a Tissue Opening

Figure 2:
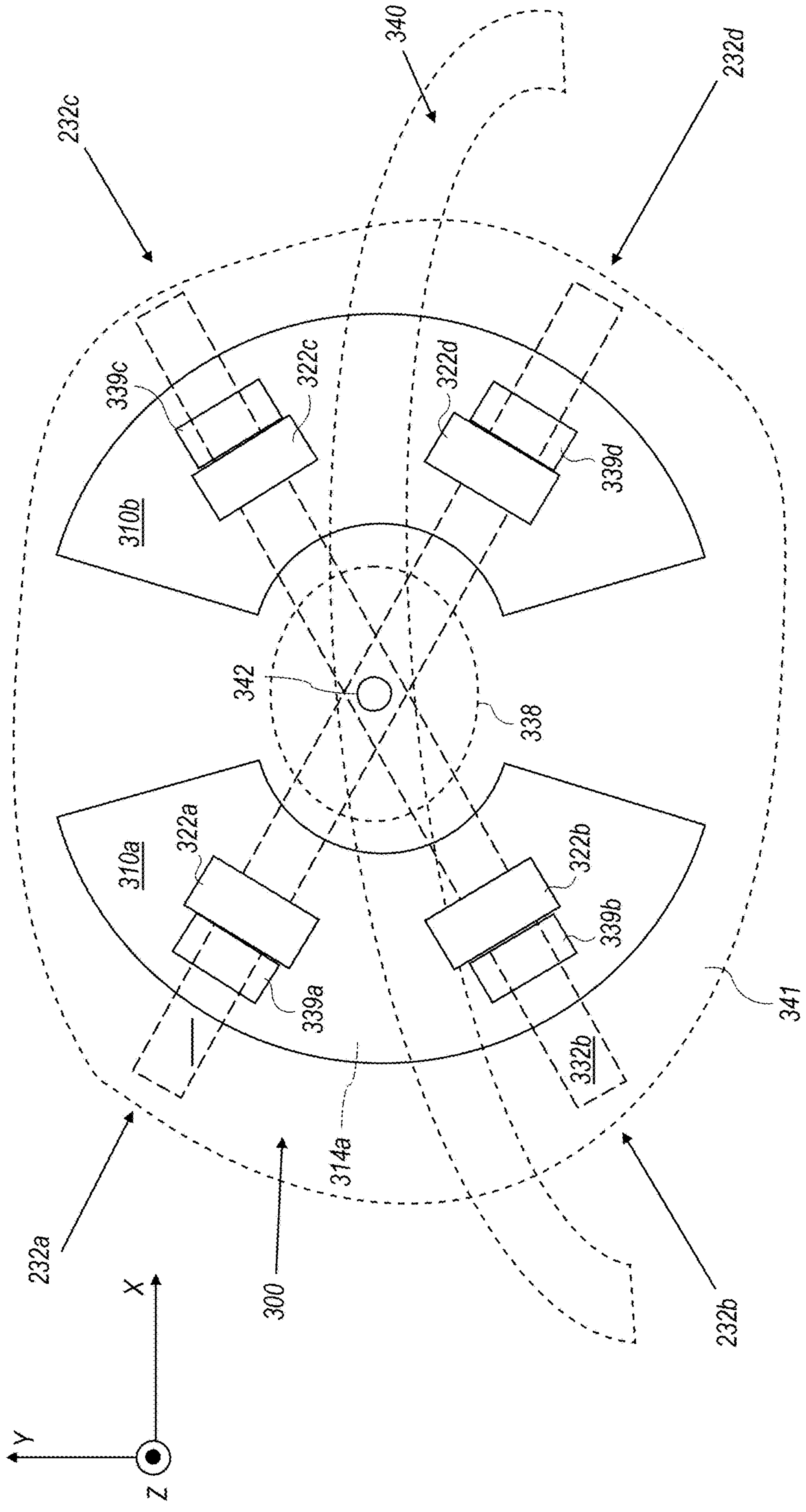
FIG. 2 illustrates a configuration of a compression device according to one configuration of the invention

FIG. 2 illustrates a compression device 300 for closing a tissue opening, such as the schematically illustrated tissue opening 338 that extends to a puncture or opening 342 in a body lumen 340, such as a vein or an artery. The compression device 300 is illustrated as including a first compression support frame 310*a* and a second compression support frame 310*b* spaced apart across the tissue opening 338. A first tension member 332*a* and a second tension member 332*b* extend between compression supports 322*a*, 322*b*, 322*c*, and 322*d* associated with, respectively, the first and second compression support frames 310*a*, 310*b*. Each of the first and second compression support frame 310*a* and 310*b* has an adhesive side 314*a*, and 314*b* configured to gather epidermal tissue 341 near the tissue opening 338.

The first and second tension members 332*a*, 332*b* have a released state and a locked state. When the first and second tension members 332*a*, 332*b* are in the released state, the first and second tension members 332*a* and 332*b* are selectively movable through the compression supports 322*a*, 322*b*, 322*c*, and 322*d*. When the first and the second tension members are in the locked state, at least a portion of the first and second tension members 332*a*, 332*b* engage the compression supports 322*a*, 322*b*, 322*c*, and 322*d* to selectively lock the tension member 332*a*, 332*b* relative to the corresponding compression supports 322*a*, 322*b*, 322*c*, or 322*d*. As such, the first and second compression support frames 310*a*, 310*b* are pushed towards the tissue opening 342 to close the tissue opening 338. The locking mechanism of engaging the portion of the tension member 332*a* or 332*b* with the compression supports 322*a*, 322*b*, 322*c*, or 322*d* will be further described later with respect to FIGS. 4A-4B and 5.

In some embodiments, each of the first and second tension members 332*a*, 332*b* includes one or more complementary structures 339*a*, 339*b*, 339*c*, 339*d*. The one or more complementary structures 339*a*, 339*b*, 339*c*, and 339*d* are configured to engage the compression supports 322*a*, 322*b*, 322*c*, and 322*d* to selectively lock the position of the first and second tension members 332*a*, 332*b* in relation to the compression supports 322*a*, 322*b*, 322*c*, and 322*d*. The locking mechanism of engaging the complementary structure 339*a*, 339*b*, 339*c*, and 339*d* with the compression supports 322*a*, 322*b*, 322*c*, or 322*d* will be further described later with respect to FIGS. 4A-5. The compressive force induced by such movement is transverse (indicated by arrows 232*a*, 232*b*, 232*c*, 232*d*) to a direction of typical manual compression force (such as a force applied perpendicular to a surface of the skin having the tissue opening 342) is sufficient to closing the tissue opening 342 without being uncomfortable to the patient.

Figure 3A:
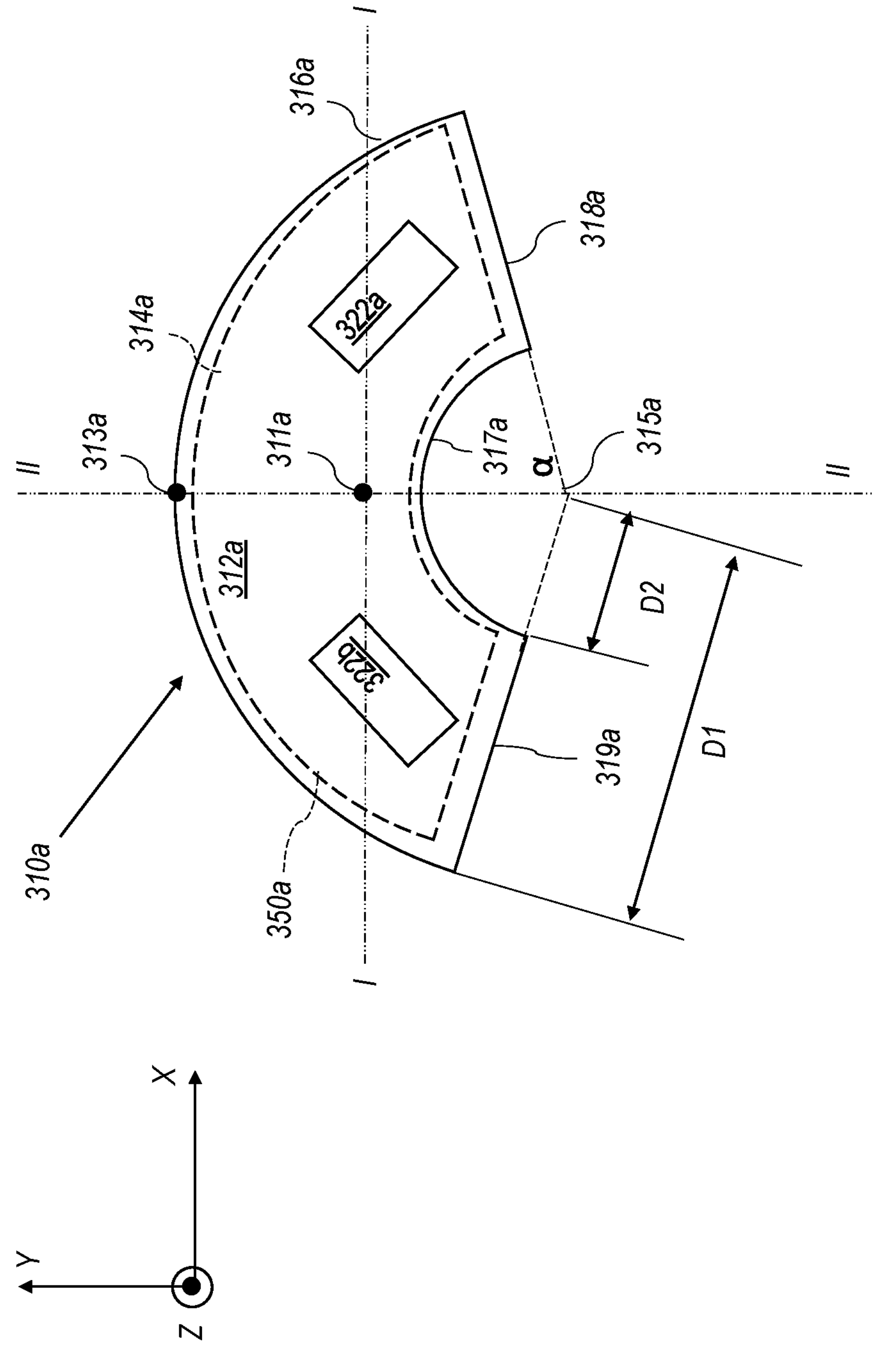

FIGS. 3A-3C illustrates a half 310*a* of a compression device 300 for closing a tissue opening. While the following discussion is directed to the compression support frame 310*a* and associated compression supports 322*a*, 322*b*, the discussion is also applicable to the compression support frame 310*b* (FIG. 2) and associated compression supports 322*c*, 322*d*.

The compression support frame 310*a* has an outer peripheral edge 316*a* forming an arc. The arc 316*a* is a part of a circle that has a center 315*a*. The central angle α of the arc 316*a* is less than 180° and greater than 45°. The compression support frame 310*a* also has an inner peripheral edge 317*a*. As illustrated in FIG. 3A, the inner peripheral edge 317*a* may also be an arc that may or may not share a same center 315*a* of a circle that the arc of the outer peripheral edge 316*a* is a part. The outer peripheral edge 316*a* has a first diameter D1, and the inner peripheral edge 317*a* has a second diameter D2, which is shorter than the first diameter D1. The compression support frame 310*a* further includes two linear edges 318*a*, 319*a* that extend between the ends of the inner peripheral edge 317*a* and the outer peripheral edge 316*a*.

The compression support frame 310*a* may be substantially planar, though in some configurations, the top side 312*a* and the bottom side 314*a* may have one or more convex portions or concave portions. The Y axis is parallel to a line I-I connecting the center 315*a* of the circle that the outer peripheral arc 316*a* is a part and a center point 313*a* of the outer peripheral arc 316*g*. Hereinafter, the direction of the Y axis is also referred to as the width direction. The X axis is parallel to a line II-II that runs through a center 311*a* of the line I-I and orthogonal to the line I-I. Hereinafter, the direction of the X axis is also referred to as the length direction. A direction of a Z axis is a direction that is orthogonal to the X-Y plane, pointing from the bottom side 314*a* toward the top side 312*a*. Hereinafter, the direction of the Z axis is also called a thickness direction.

The compression support frame 310*a* may be substantially planar, though in some configurations, the top side 312*a* and the bottom side 314*a* may have one or more convex portions or concave portions. The Y axis is parallel to a line I-I connecting the center 315*a* of the circle that the outer peripheral arc 316*a* is a part and a center point 313*a* of the outer peripheral arc 316*a*. Hereinafter, the direction of the Y axis is also referred to as the width direction. The X axis is parallel to a line II-II that runs through a center 311*a* of the line I-I and orthogonal to the line I-I. Hereinafter, the direction of the X axis is also referred to as the length direction. A direction of a Z axis is a direction that is orthogonal to the X-Y plane, pointing from the bottom side 314*a* toward the top side 312*a* Hereinafter, the direction of the Z axis is also called a thickness direction.

The compression device 300 also includes one or more compression support(s) 322*a*, 322*b* mounted to the compression support frame 310*a*. The one or more compression supports 322*a*, 322*b* can be fixedly or movably mounted to the compression support frame 310*a*. For instance, in some configurations, the one or more compression support(s) 322*a*, 322*b* are rotatably mounted to the compression support frame 310*a*, such that the compression support 322*a*, 322*b* is configured to rotate based on a tension force applied by the tension member 332*a*, 332*b*.

FIG. 3C illustrates a side view of the compression device applied on epidermal tissue 341 for closing a tissue opening 342 disposed thereon. As schematically illustrated in FIG. 3C, a pin or protrusion 326 can extend from the top surface of the compression support frame and the compression support is interference fit to the pin or protrusion 326, while allowing rotational movement of the compression support in relation to the pin or protrusion. For instance, the pin or protrusions 326 can include a detent 328 that is received within a complementary groove or capture structure 330 formed within a receiving recess 336 of the compression support. In some embodiments, the tension member 332*a*, 332*b* includes a flexible elongate member 333*a*, 333*b* and one or more complementary structures 339*a*, 339*b* to lock the flexible elongate member 333*a*, 333*b* in place.

As illustrated in FIG. 3B, the compression device 300 also includes one or more tension member(s) 332*a*, 332*b* selectively slidable in relation to the compression support 322*a*, 322*b*. In some configurations, the compression support 322*a*, 322*b* may be a ring-shaped or a tubular-shaped piece that has an opening 324. In some other configurations, the compression support 322*a*, 322*b* may be a half-ring-shaped or a half-tubular-shaped piece that has a semi-circular-shaped opening. In some configurations, the compression support 322*a*, 322*b* may be a soft fabric ring. The opening 324 of the compression support 322*a*, 322*b* is configured to at least accommodate the elongate member 333*a*, 333*b* of the tension member 332*a*, 332*b*.

Figure 4A:
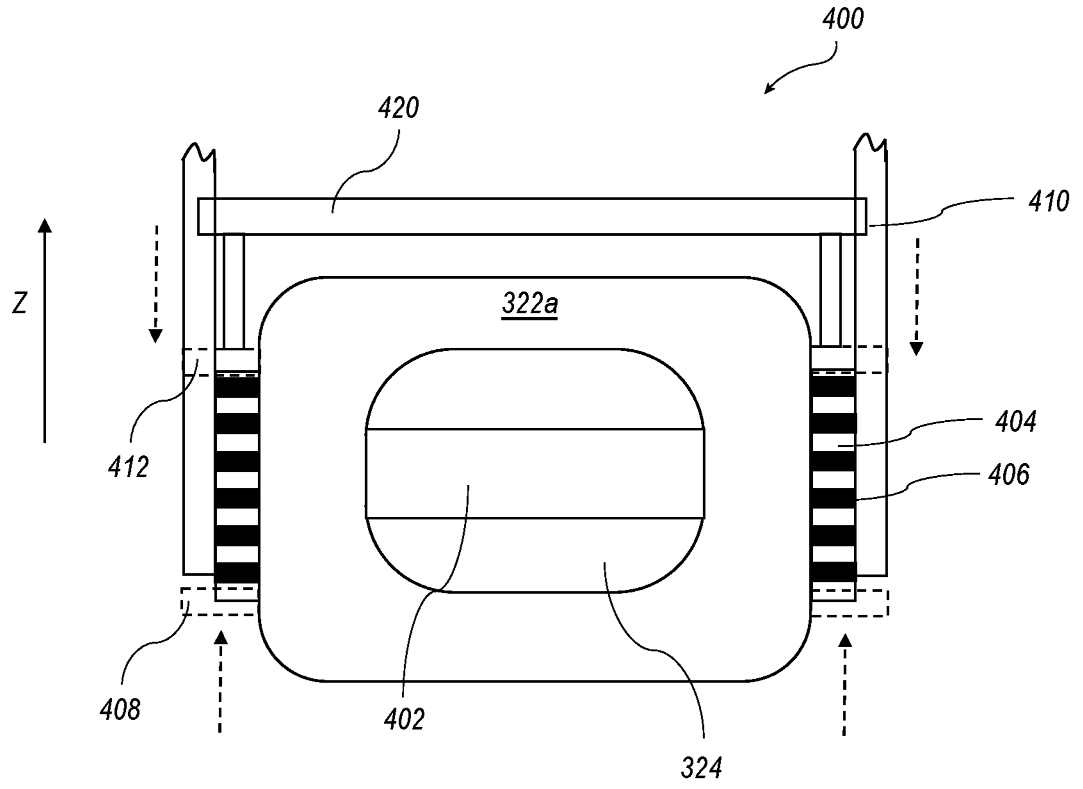
FIGS. 4A-4B illustrates a locking mechanism of the compression device according to configurations of the invention.
Figure 4B:
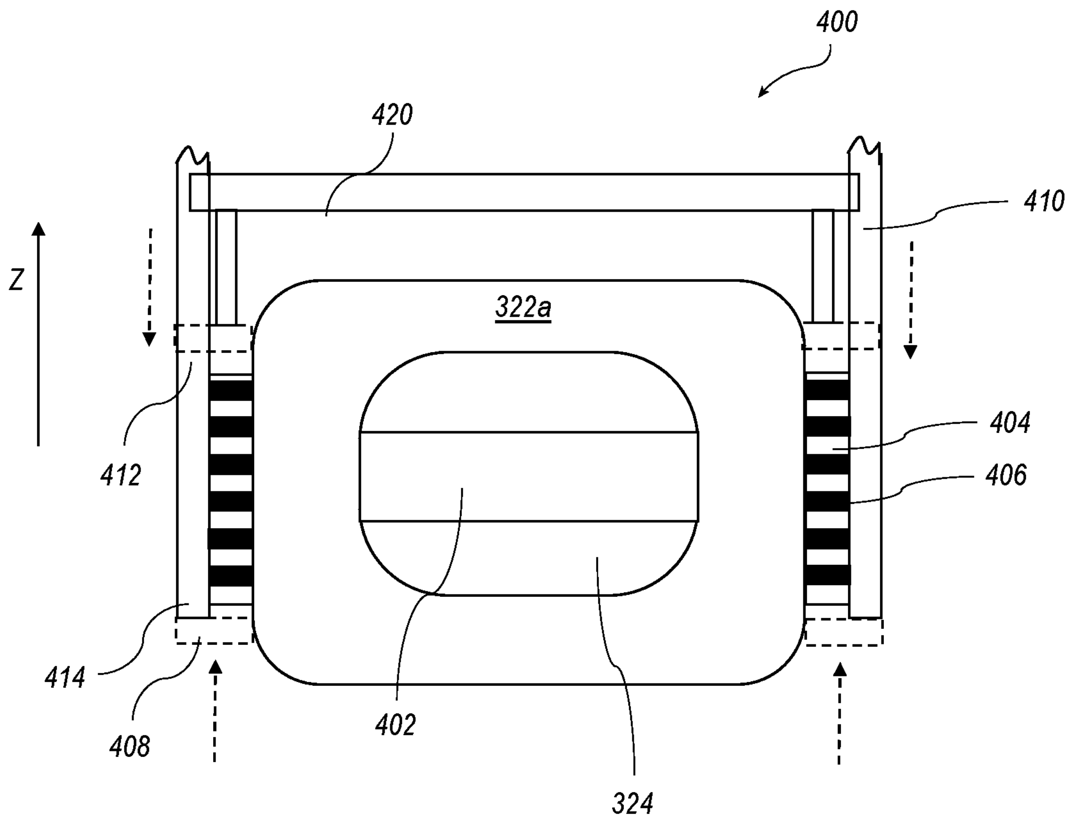

In some configurations, the opening 324 of the compression support 322*a*, 322*b* is sufficiently large to accommodate a portion of a ratchet mechanism 400 that selectively receives and engages with the tension member 332. For instance, as illustrated in FIGS. 4A and 4B, the ratchet mechanism 400 includes a mandrel 402 that cooperates with the tension member 332. The mandrel 402 may have a rough surface configured to use the friction between the rough surface and the tension member to cause the tension member to move with the mandrel 402. For instance, the mandrel 402 can have teeth or serrations the engage with the material forming the tension member 332 or engage with preformed structures, such as complementary teeth or serrations, of the tension. In some embodiments, the mandrel 402 may have a polygon-shaped cross-section, such that the edges of the polygon shape generate the friction to cause the tension member 332 to move with the mandrel 402.

Ratchet wheels 404, with cams 406, cooperate with a pawl 408 mounted in an actuator handle 410 and a pawl 412 mounted to the compression support 322*a*, 322*b*. With both pawls 408, 412 biased towards the ratchet wheels 404 (as illustrated by the dotted arrows), rotation of the actuator handle 410 in one direction rotates the mandrel 402 through engagement between the pawl 412 and the cams 406, while such engagement also prevents reverse rotation of the mandrel 402. Reverse rotation of the mandrel 402 can be achieved by disengaging the pawls 408, 412 from the ratchet wheels 404 through overcoming the biasing force, as illustrated in FIG. 4B. Moving the actuator handle 410 to an open state, such as through rotation of the actuator handle 410, positions an enlarged end 414 of the actuator handle 410 to engage the pawl 408 and displace it away from the ratchet wheels 404 by overcoming the bias force. Manipulating an actuator arm 420 to move the pawl 412 away from the ratchet wheels 404 allows the mandrel 402 to freely move within the compression support 322*a*, 322*b*. The actuator arm 420 can slidably cooperate with the actuator handle 410 and withdraw the pawl 412, and optionally displaces the pawl 412 in a locking position that prevents unwanted movement of the actuator handle 410.

Figure 5:
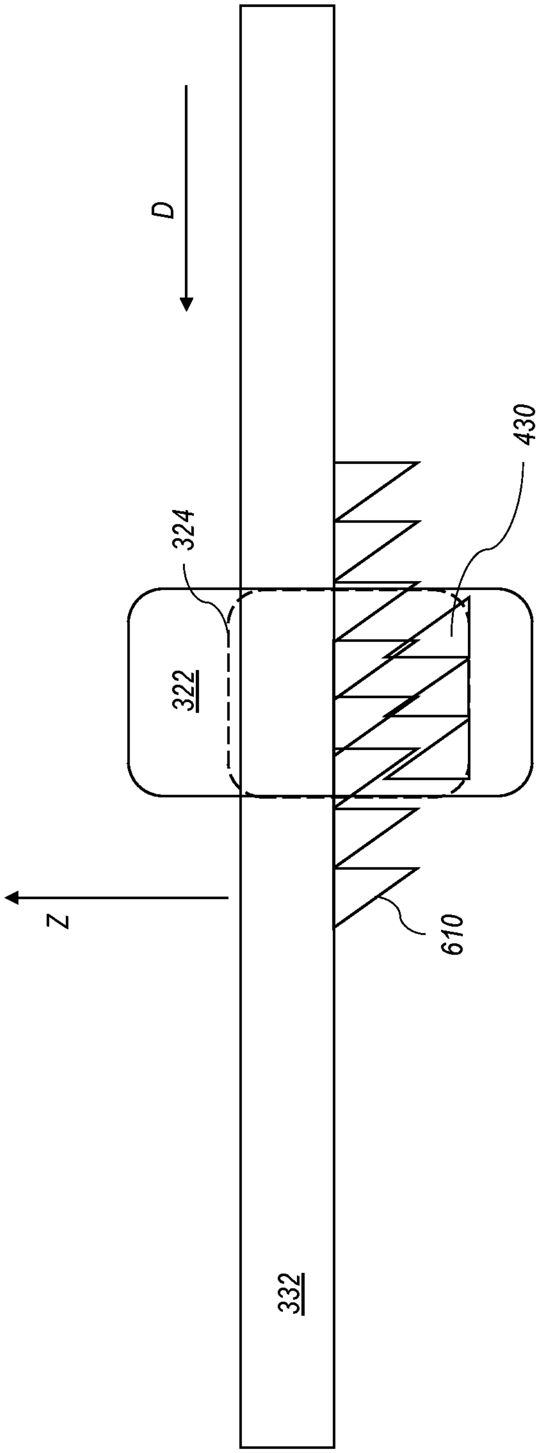
FIG. 5 illustrate a locking mechanism of the compression device according to configurations of the invention.

FIG. 5 further illustrates another configuration of the locking mechanism. As illustrated in FIG. 5, there are one or more teeth or serrations 430 on at least a portion of the inner surface of the opening 324 of the compression support 322. Further, at least a portion of the tension member 332 also has a plurality of complementary teeth or serrations 610, which constitutes, in one configuration, a complementary structure 339. The teeth or serrations 430 and 610 engage with each other to cause the tension member 332 to be able to slide through the opening 324 in only one direction D.

In some configurations, the elongate member of the tension member 332 or at least a portion thereof is made from stretch fabric or material. In particular, the elongate member of the tension members may be made from one or more of the following: polymeric materials, metallic materials (such as, but not limited to, corrosion-resistant steels), a combination of polymeric and metallic materials, nylon, polycarbonate, fluoropolymer, glass, and/or carbon fiber reinforcement. In some configurations, the elongate member of the tension members may be made via wire cable inserted molding. In some configurations, the tension member 332 further includes a tension control mechanism, such that the tension force applied onto the tension member 332 cannot exceed a predetermined threshold, and when the tension member 332 is tightened to cause the tension to reach the predetermined threshold, the tension control mechanism prevents the tension member 332 from being further tightened. For example, in some embodiments, the tension force may be controlled by the shape of the ratcheting wheel 404 and the shape of the pawls of FIGS. 4A-4B and 5. In some embodiments, the tension force may be controlled by the shapes of the serrations of FIG. 5. In some embodiments, the tension member 332 may also include a tension adjustment mechanism configured to accurately control the amount of tension applied to the tension member 332. For example, a range of tension applied to the tension member may be between 10 Newton (2.24 lbf) to 100 Newtons (22.5 lbf). While specific configurations of the locking mechanism are illustrated, it will be understood that combinations and/or modifications of the illustrated configurations are also possible and contemplated by the present disclosure.

Figure 6A:
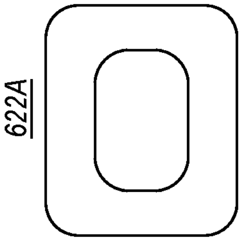
FIGS. 6A-6G illustrate configurations of a compression support frame having a plurality of portions on the tissue contact side of the compression support frame according to configurations of the invention.
Figure 6B:
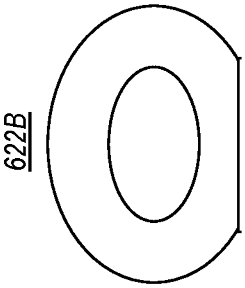
Figure 6C:
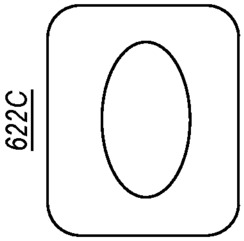
Figure 6D:
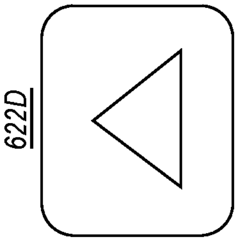
Figure 6E:
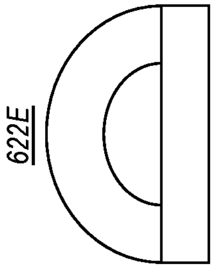
Figure 6F:
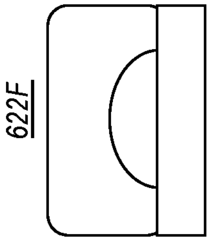
Figure 6G:
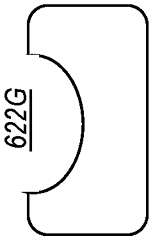

FIGS. 6A through 6G illustrate various configurations of the compression support 322. FIG. 6A illustrates a configuration of the compression support 622A that has a round-cornered rectangular outer surface and inner surface. FIG. 6B illustrates a configuration of the compression support 622B that has a substantially oval-shaped outer surface and inner surface. The bottom of the compression support 622A may have a flat bottom configured to merge with the top side of the compression support frame. FIG. 6C illustrates a configuration of the compression support 622C that has a round-cornered rectangular outer surface and an oval-shaped inner surface. FIG. 6D illustrates a configuration of the compression support 622D that has a round-cornered rectangular outer surface and a triangular inner surface. FIG. 6E illustrates a configuration of the compression support 622E that has an arched outer surface and an arched inner surface. FIG. 6F illustrates a configuration of the compression support 622F that has a round-cornered rectangular outer surface and an arched inner surface. FIG. 6G illustrates a configuration of the compression support 622G that has a concaved top side. While specific configurations of the compression support are illustrated, it will be understood that combinations and/or modifications of the illustrated configurations are also possible and contemplated by the present disclosure.

The one or more compression support(s) 322 may be mounted at various positions and/or orientations of the top side or edges of the compression support(s) 322. Referring back to FIGS. 3A and 3B, two compression support(s) 322*a*, 322*b* are positioned symmetrically along the line II-II. As illustrated, the two compression support(s) 322*a*, 322*b* are positioned in a direction, such that when the tension members 332*a*, 332*b* are inserted into the tension members 332*a*, 332*b*, the tension members 332*a*, 332*b* passes through the center 315 of the circle that the outer peripheral arc 316 is a part. FIGS. 3A and 3B merely illustrate one example configuration. Additional configurations may also be implemented to achieve the same or similar functions.

Figures 7A, 7B, 7C, 7D:
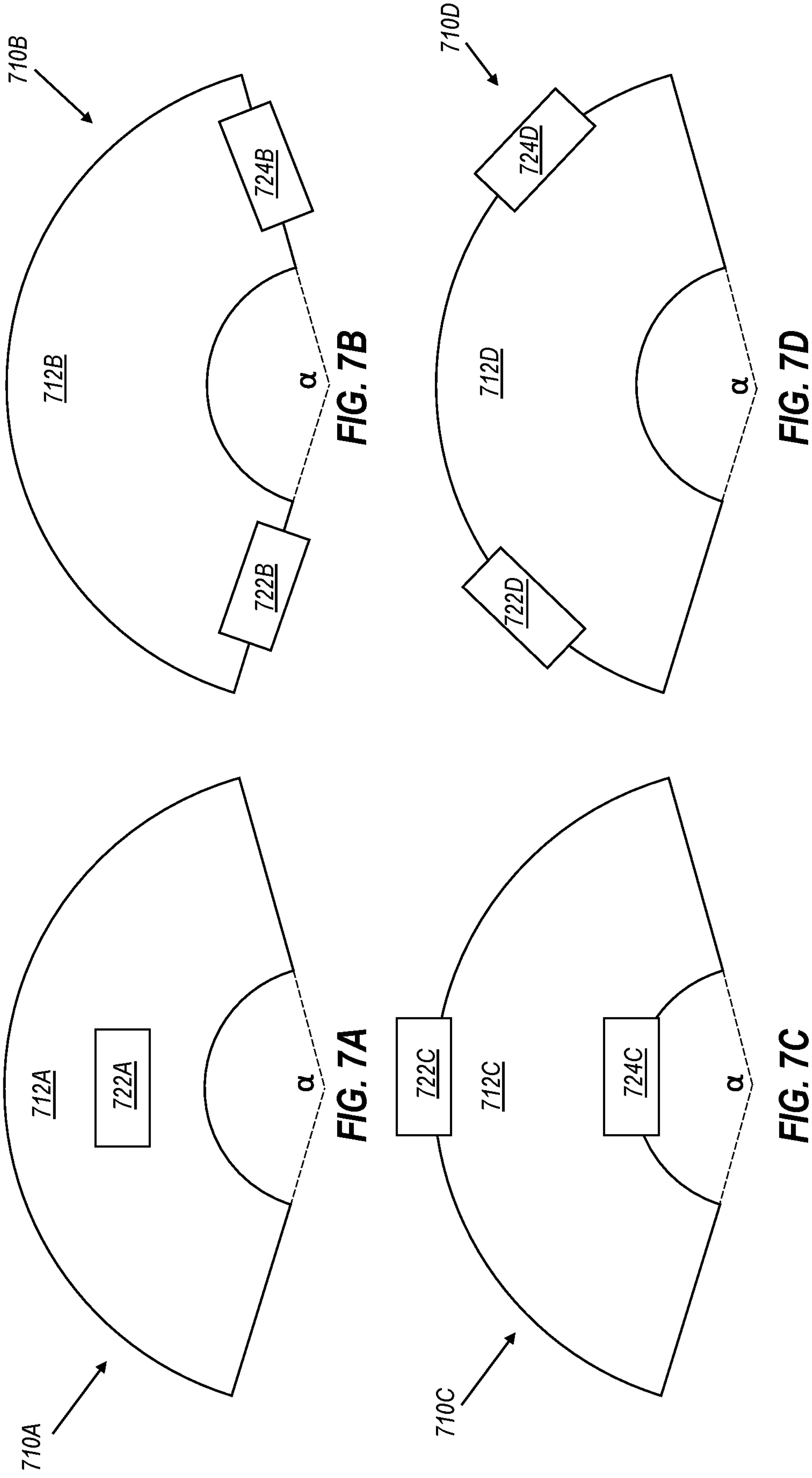
FIGS. 7A-7D illustrate alternate compression devices according to configurations of the invention.

FIGS. 7A through 7D illustrate a few different configurations, in which the compression support(s) are mounted at different positions. FIG. 7A illustrates a configuration of the compression support frame 710A that has a single compression support 722A mounted on the top side 712A of the compression support frame 710A. FIG. 7B illustrates a configuration of the compression support frame 710B that has two compression supports 722B and 724B, each of which is mounted on a linear side of the compression support frame 710B on a top side 712B of the compression support frame 710B. FIG. 7C illustrates a configuration of the compression support frame 710C that has two compression supports 722C, 724C, each of which is mounted at an outer peripheral edge or an inner peripheral edge of the compression support frame 710C on a top side 712C of the compression support frame 710C. FIG. 7D illustrates a configuration of the compression support frame 710D that has two compression supports 722D, 724D, both of which are mounted on the outer peripheral edge of the compression support frame 710D on a top side 712D of the compression support frame 710D. When the compression support 722, 724 is mounted on the edge of the compression support frame, the opening of the compression support 722, 724 may be in a direction along the X-Y plane or in the direction of Z axis. While specific positions of the compression supports are illustrated, it will be understood that combinations and/or modifications of the illustrated configurations are also possible and contemplated by the present disclosure.

As previously described, the bottom side 314 of the compression support frame 310 includes adhesive 350 that is configured to be attached to an area surrounding a vascular access site to gather the epidermal tissue. When the tension member(s) 332*a*, 332*b* is tightened between the two compression supports (e.g., 322*a*, 322*d*), the adhesive 350 is configured to push or pull the gathered epidermal tissue toward the tissue opening 342 to close the tissue opening 342, while keeping the patient as comfortable as possible. To achieve this goal, the bottom side 314 of the compression support frame 310 having the adhesive 350 may be formed in a particular shape. In some configurations, at least a portion of the bottom side 314 is planar, such that the compression support frame 310 can be easily attached to the skin of the patient and gather a large area of flat epidermal.

Figure 8B:
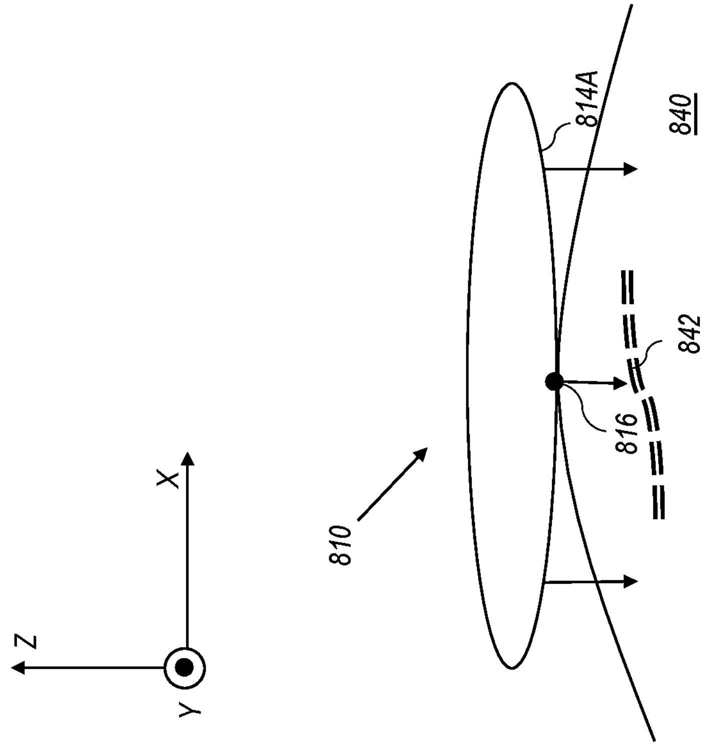
FIGS. 8A-8B illustrate an alternate compression device according to configurations of the invention.
Figure 8A:
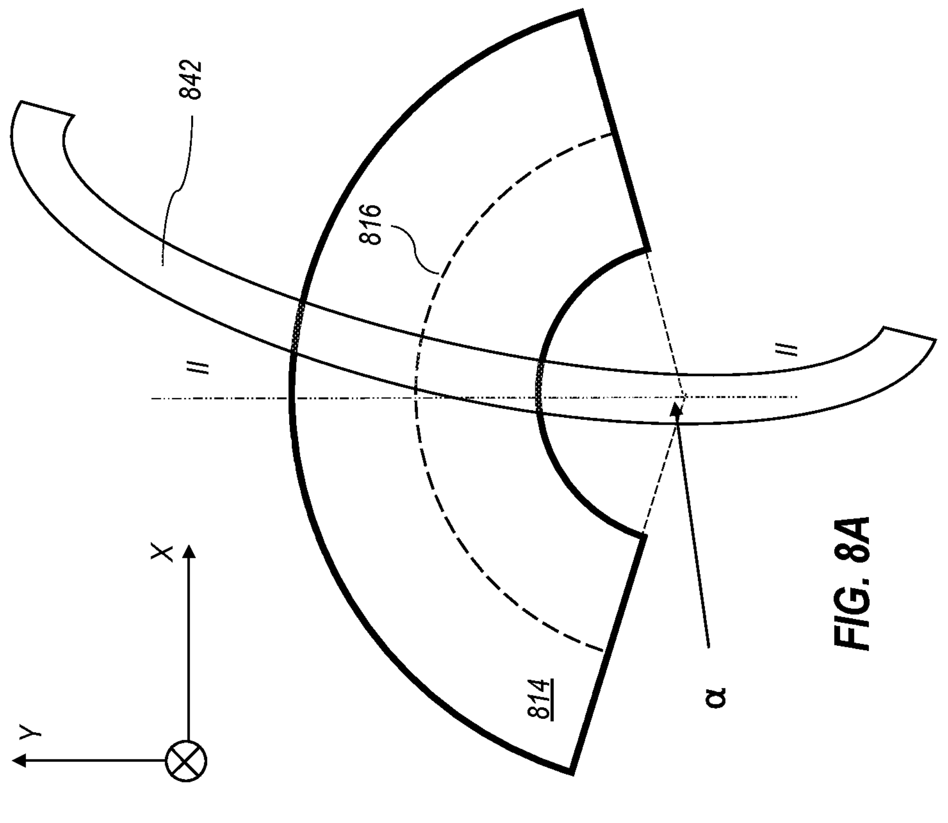

In some configurations, the bottom side 314 is a convex-shaped surface that applies an even force to the epidermal tissue around the vascular access site evenly. The curved surface also prevents the edge of the compression support frame 310 from scratching or cutting the epidermal tissue when the epidermal tissue is compressed. FIGS. 8A-8B illustrate such a configuration. FIG. 8A illustrates a bottom side 814 of the compression support frame 810 that has a convex-shaped surface, such that the bottom side 814 protrudes along a middle arc 816. FIG. 8B illustrates a cross-sectional view of the compression support frame 810 taken along line II-II. As illustrated in FIG. 8B, when the bottom side 814A of the compression support frame 810 is pressed down onto an area of tissue 840, the force applied onto the area of tissue is the highest along the middle arc 816, and the force gradually tapers from the middle arc 816 to the inner peripheral edge and outer peripheral edge of the bottom side 814 of the compression support frame 810. In particular, part of the tissue on top of the vein or the artery 842 that has the opening is pressed by the convex shaped bottom side 814A. Since the compression support frame 810 is an arc shaped, regardless of which direction the vessel 842 is positioned, the compression support frame 810 is capable of pressing an area of the tissue directly on top of the vessel 842.

Figure 9A:
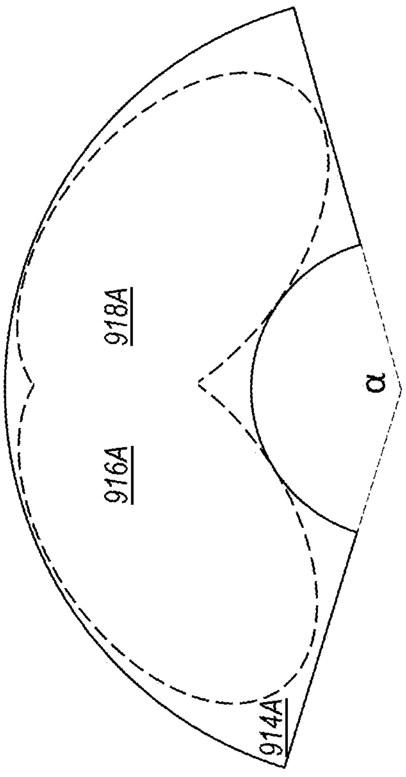
FIGS. 9A-9D illustrate various tissue side configurations of the compression device according to configurations of the invention.

FIGS. 8A-8B merely illustrate one configuration of the bottom side 814. Different configurations may also be implemented to achieve similar functions. FIGS. 9A-9D illustrate various configurations of the bottom side 914 of the compression support frame. FIG. 9A illustrates a configuration of the bottom side 914A that has two convex portions 916A and 918A along the arc of the compression support frame 910A. FIG. 9C illustrates a configuration of the bottom side 914C that has three convex portions 916C, 917C, 919C along the arc of the compression support frame 910C. Any number of convex portions may be implemented at the bottom side 914 along the arc of the compression support frame 910C or in any other direction. Each of the convex portions 916A-918A, 916C-919C may be shaped similarly as human fingertips to apply forces similarly applied by human fingers in manual compression. Additionally, the convex portions can be positioned and oriented to increase the efficacy of the forces applied by tensioning the tension members. While specific configurations of the convex portions are illustrated, it will be understood that combinations and/or modifications of the illustrated configurations are also possible and contemplated by the present disclosure.

Figure 9B:
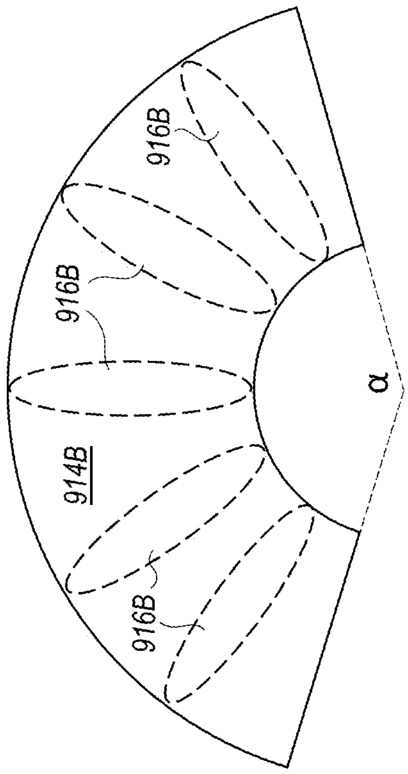
Figure 9C:
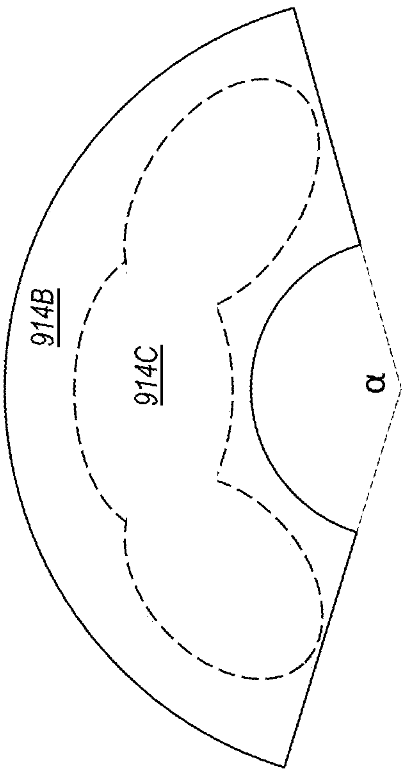
Figure 9D:
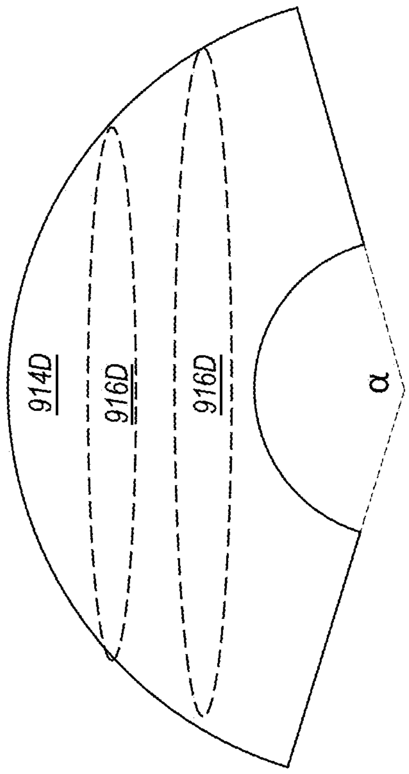

FIGS. 9B and 9D illustrate two additional configurations of the bottom side 914 of the compression support frame 910B. Referring to FIG. 9B, the bottom side 914B of the compression support frame 910B has a plurality of elongate convex portions or protrusions 916B, each of which is along the directions between the center of the circle that the outer peripheral edge is a part and a point of the outer peripheral edge. Referring to FIG. 9D, the bottom side 914D of the compression support from 910D has a plurality of elongated convex portions or protrusions 916D, each of which is in the length X direction. Additionally, the convex portions can be positioned and oriented to increase the efficacy of the forces applied by tensioning the tension members. While specific configurations of the convex portions are illustrated, it will be understood that combinations and/or modifications of the illustrated configurations are also possible and contemplated by the present disclosure.

Similar to the bottom side 314, the top side 312 of the compression support frame 310 may also be formed in different shapes, e.g., flat or with various convex or concave portions. FIGS. 10A-10F further illustrate cross-sectional views of the compression support frame taken along the line II-II of FIGS. 3A-3B, which shows both the top side 1012 and the bottom side 1014. While specific configurations are illustrated, it will be understood that combinations and/or modifications of the illustrated configurations are also possible and contemplated by the present disclosure.

Figure 10A:
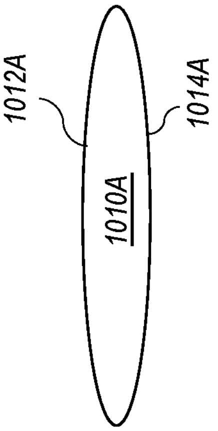
FIGS. 10A-10F illustrate various alternate top side configurations of the compression device according to configurations of the invention.
Figure 10B:
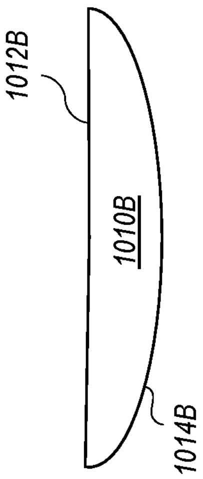
Figure 10C:
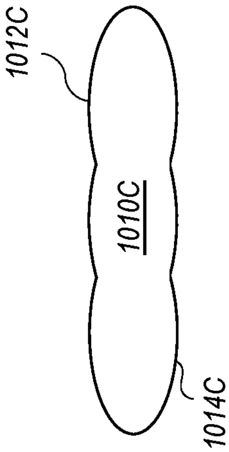
Figure 10D:
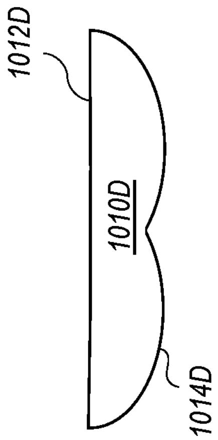
Figure 10E:
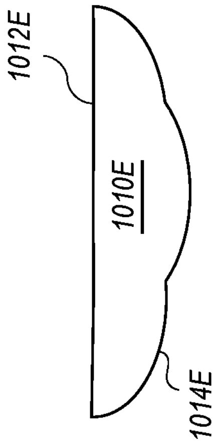
Figure 10F:
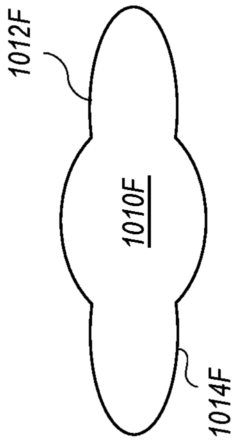

FIG. 10A illustrates a configuration of the compression support frame 1010A that has a concave top side 1012A and a convex bottom side 1014A. FIG. 10B illustrates a configuration of the compression support frame 1010B that has a flat top side 1012B and a convex bottom side 1014B. FIG. 10C illustrates a configuration of the compression support frame 1010B that has three similar height convex portions in each of the top side 1012C and 1014C. FIG. 10D illustrates a configuration of the compression support frame 1010D that has a flat top side 1012D and a bottom side 1014D having two convex portions. FIG. 10E illustrates a configuration of the compression support frame 1010E that has flat top side 1012E and a bottom side 1014E having 3 convex portions, among which a center convex portion protrudes further than the other two convex portions. FIG. 10F illustrates a configuration of the compression support frame 1010F that has a bottom side 1014F similar to the bottom side 1014E of FIG. 10E. However, unlike the compression support frame 1010E of FIG. 10E that has a flat top, the top side 1012F of FIG. 10F has a top side 1012F that has three convex portions, among which a center convex portion protrudes further than the other two convex portions.

Generally, the compression support frame may be made from one or more of the following: polymeric materials (such as, but not limited to acetal, polycarbonate, PETG, HDPE, polypropylene), or a combination of polymer and metallic materials. Such materials may be glass or carbon fiber reinforced. In some configurations, the compression support(s) may be made from the same material of the compression support frame, and the compression support frame and the compression support(s) may be integrated as a single piece. In some configurations, the compression support(s) may be made from different materials of the compression support frame and attached to the compression support frame during manufacturing or at the time of use. Generally, the adhesive layer may be made from organic or inorganic materials. In some configurations, the adhesive is rubber, acrylic, and/or silicon-based. In some configurations, the adhesive layer is about 1 mm to 2.5 mm thick. In some configurations, in addition to adhesive, the compression frame may have microneedles to facilitate stability on the epidermis.

Generally, the length of the compression support frame is wider than a diameter of the procedural sheath for closure. For example, for an access site of up to 26-French catheter, the length of the compression support frame is between a range of about 40 mm to about 50 mm, the width of the compression support frame is between a range of about 20 mm to about 30 mm, the diameter of the circle, of which the outer peripheral arc is a portion, is between a range of about 30 mm to about 40 mm, and the diameter of the circle, of which the inner peripheral arc is a portion, is between a range of about 12 mm to about 20 mm.

III. Method of Using the Compression Device

The compression device described herein may be used to compress a vascular access site for closing the tissue opening caused by the vascular access. First, one or more compression support frame(s) is attached to an area of tissue surrounding the vascular access site prior to the vascular access. Referring to FIG. 2, two compression support frames 310*a* and 310*b* are applied on an area of tissue surrounding a vascular access site 342 of a patient. Those compression devices 310*a*, 310*a* can be positioned pre- or post-medical procedure performance through the vascular access site 342, which provides access to the patient's vasculature. Each of the compression devices 310*a* and 310*b* is placed on an opposite side of the vascular access site 342. Since the compression support frames 310*a* and 310*b* are arc-shaped, the compression force applied to the epidermal tissue surrounding the vascular access site 342 is substantially evenly distributed. Thus, the compression devices 310*a* and 310*b* can be positioned in any direction relevant to the blood flow of the vessel.

The compression support frame 310*a* has two compression support 322*a* and 322*b*, and the compression support frame 310*b* has two compression support 322*c* and 322*d*. A first tension member 332*a* is inserted through the compression support 322*a* of the compression device 310*a*, and the compression support 322*d* of the compression device 310*b*. A second tension member 332*b* is inserted through the compression support 322*c* of the compression device 310*b*, and the compression support 322*b* of the compression device 310*a*. As such, the first tension member 332*a* and the second tension member 332*b* are positioned diagonally to allow the tension force applied onto the compression support frames 310*a*, 310*b*, which, in turn, passes on to the epidermal tissue via the adhesive 350*a*, 350*b*, to be evenly distributed along the arcs of the compression support frames 310*a*, 310*b*.

After the vascular access, each of the tension members 332*a* and 332*b* is tightened to apply a tension force onto the compression support frames 310*a*, 310*b* across directions pointing to the tissue opening 342, which are indicated by the arrows 232*a*, 232*b*, 232*c*, and 232*d*. As such, the tension force applied onto each of the compression support frames 310*a* and 310*b* is distributed substantially evenly to close the tissue opening and also keep the patient comfortable. The tension members 332*a* and 332*b* may be kept in the tightened state for a predetermined period that is between a range of about 15 minutes to about 600 minutes, before releasing them, depending on the vessel access site, the size of the access, the user of antiplatelet therapy, and/or the patient's condition and needs. Generally, for a small access site, the application period of the compression device could be in the range of about 60 minutes to as high as about 380 minutes.

Figure 11:
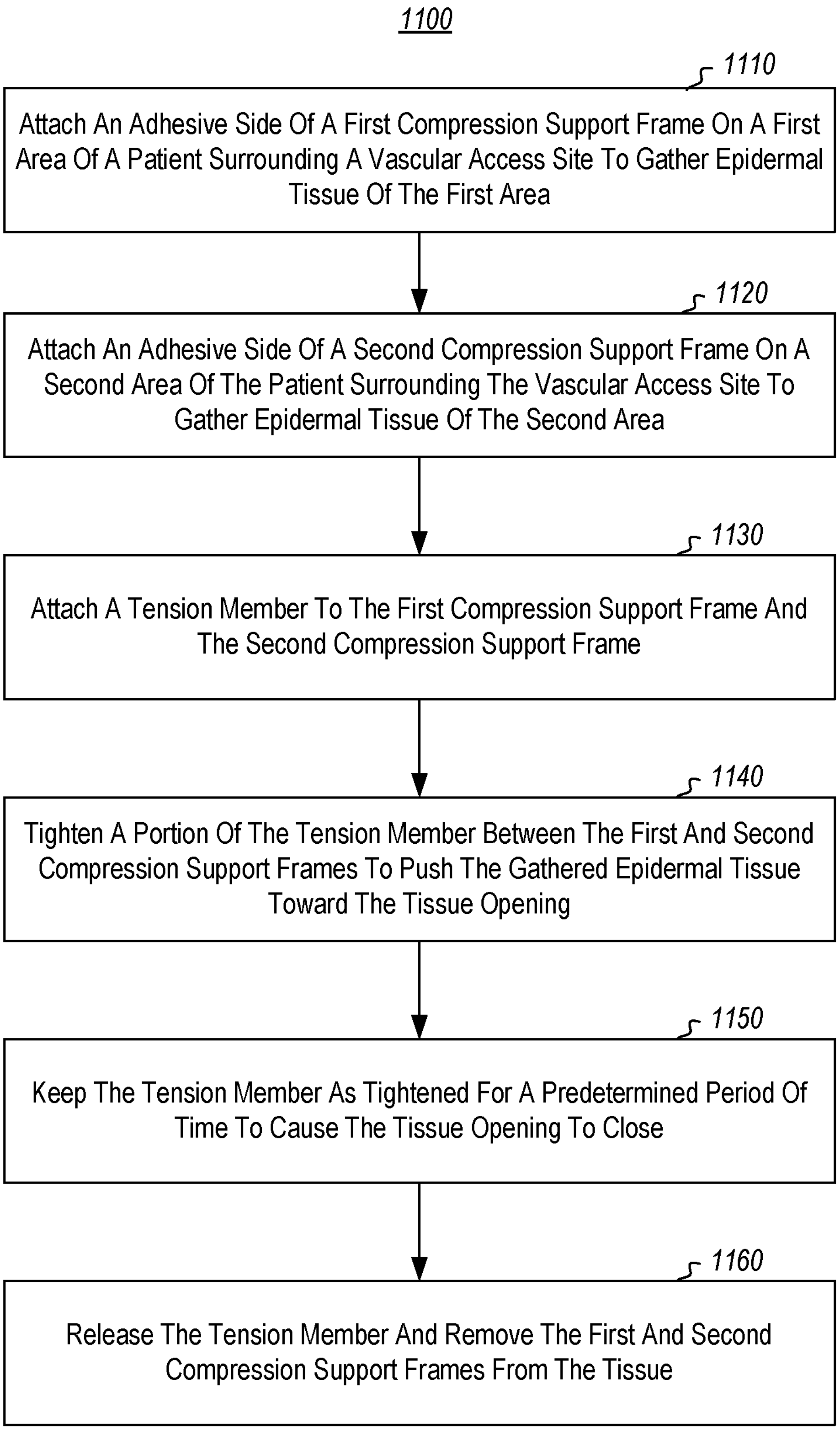
FIG. 11 is a flowchart of an example method for closing the tissue opening according to a method of the present invention.

FIG. 11 illustrates a flowchart of an example method 1100 for using a plurality of compression support frames to close a tissue opening. The method 1100 includes attaching an adhesive side of a first compression support frame on a first area of a patient surrounding a vascular access site to gather epidermal tissue of the first area (act 1110). The method 1100 further includes attaching an adhesive side of a second compression support frame on a second area of the patient surrounding the vascular access site to gather epidermal tissue of the second area (act 1120). Each of the first area and second area is on an opposite side of the vascular access site. Note, the attachment of the adhesive side of the first or second compression support frames may be performed before, during, and/or after the vascular access.

Thereafter, a tension member is attached to both the first compression support frame and the second compression support frame (act 1130). After the vascular access procedure is completed, a portion of the tension member between the first compression support frame and the second compression support frame is tightened to cause the first and second compression support frames to push or pull the gathered epidermal tissue toward the access site (act 1140). Since the tension member is attached to both the first compression support frame and the second compression support frame, the tension force generated by the tension member is substantially evenly applied onto both the first compression support frame and the second compression support frame towards the access site to provide better closure result and comfort to the patient. The tension member is kept as tightened for a predetermined period of time (e.g., 15-45 minutes) to cause the tissue opening to close (act 1150). Finally, the tension member is released, and the first and second compression support frames are released from the tissue of the patient (act 1160).

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

Following are some further example embodiments of the invention. These are presented only by way of example and are not intended to limit the scope of the invention in any way. Further, any example embodiment can be combined with one or more of the example embodiments.

Embodiment 1. A device for closing a tissue opening. The device includes a compression support frame having an outer peripheral edge forming an arc whose central angle is less than 180° and greater than 45°. The device also includes a compression support mounted to the compression support frame and a tension member selectively slidable in relation to the compression support.

Embodiment 2. The device of embodiment 1, wherein the central angle is less than about 180° and greater than about 60°.

Embodiment 3. The device of any of embodiments 1-2, wherein the central angle is less than about 150° and greater than about 90°.

Embodiment 4. The device of any of embodiments 1-3, wherein the compression support is rotatably mounted to the compression support frame.

Embodiment 5. The device of any of embodiments 1-4, wherein the compression support frame comprises a body having an adhesive configured to be adhered on a tissue contact side of the body.

Embodiment 6. The device of any of embodiments 1-5, wherein the compress support comprises an opening to accommodate the tension member.

Embodiment 7. The device of any of embodiments 1-6, wherein the compression support comprises an opening to accommodate the tension member and a pawl to releasably engage complementary structures on the tension member.

Embodiment 8. The device of any of embodiments 1-7, wherein the complementary structures comprise teeth formed in the tension member.

Embodiment 9. A device for closing a tissue opening. The device includes a compression support frame having an outer peripheral edge forming an arc whose central angle is less than 180° and greater than 45°. The device also includes a plurality of compression supports mounted to the compression support frame and a plurality of tension members, each of which is selectively slidable in relation to at least two compression supports of the plurality of supports.

Embodiment 10. The device of embodiment 9, wherein the central angle is less than about 180° and greater than about 60°.

Embodiment 11. The device of any of embodiments 9-10, wherein the central angle is less than about 150° and greater than about 190°.

Embodiment 12. The device of any of embodiments 9-11, wherein the compression support is rotatably mounted to the compression support frame.

Embodiment 13. The device of any of embodiments 9-12, wherein the compression support frame comprises a body having an adhesive configured to adhere on a tissue contact side of the body.

Embodiment 14. The device of any of embodiments 9-13, wherein each of the plurality of compression supports includes an opening to accommodate the tension member and a pawl to releasably engage complementary structures on the tension member.

Embodiment 15. The device of any of embodiments 9-14, the complementary structures include teeth formed in the tension member.

Embodiment 16. A method for compressing an area of tissue of a patient for closing a tissue opening. The method includes attaching an adhesive side of a first area of tissue of a patient surrounding a vascular access site to gather epidermal tissue of the first area, and attaching an adhesive side of a second compression support frame on a second area of the patient surrounding the vascular access site to gather epidermal tissue of the second area. Next, a first tension member is attached to the first compression support frame and the second compression support frame. A portion of the first tension member between the first compression support frame and the second compression support frame is tightened to push the gathered epidermal tissue toward the tissue opening, and the first tension member is kept tightened for a predetermined period of time to cause the issue opening to close. Finally, the first compression support frame and the second compression support frame are removed from the respective first area and second area of tissue.

Embodiment 17. The method of embodiment 16, the pressure applied to the first area and second area of tissue surrounding the vascular access site is controlled at a range between 2 lbf (8.9 Newtons) to 12 lbf (53.4 Newtons).

Embodiment 18. The method of any of embodiments 16-17, wherein the first area or the second area is upstream or downstream from the vascular access site based on a direction of the blood flow.

Embodiment 19. The method of any of embodiments 16-18, further includes attaching a second tension member to both the first compression support frame and the second compression support frame, and tightening a portion of the second tension member between the first compression support frame and the second compression support frame to push the gathered epidermal tissue toward the tissue opening.

Embodiment 20. The method of any of embodiment 19, wherein the first tension member and the second tension member intersect each other.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A device for closing a tissue opening, the device comprising:

a compression support frame configured to contact tissue surrounding the tissue opening, the compression support frame comprising an arc-shape with a first linear edge, a second linear edge, an inner peripheral edge extending between the first linear edge and the second linear edge, and an outer peripheral edge extending between the first linear edge and the second linear edge, forming part of a circle having a dimension D1 from a center of the circle to the outer peripheral edge, and forming a continuous arc whose central angle is less than 180° and greater than 45° and whose dimension D1 is constant over the outer peripheral edge, the compression support frame having a top surface disposed in a first plane, a bottom of the compression support frame comprising a plurality of elongate protrusions each having a long axis and a short axis as viewed in a direction perpendicular to the first plane, the long axis of each of the plurality of elongate protrusions extending transversely to the dimension D1 of the compression support frame and extending from the inner peripheral edge to the outer peripheral edge of the compression support frame;

a compression support mounted to and extending from the top surface of the compression support frame, the compression support being rotatably mounted to an elongated protrusion extending from the top surface of the compression support frame, an axis of rotation of the elongated protrusion being perpendicular to the first plane of the compression support frame; and a tension member selectively slidable in relation to the compression support to rotate the compression support about the compression support frame, wherein the compression support is configured to rotate based on a tension force applied by the tension member, the arc-shape of the compression support frame evenly distributing the tension force applied by the tension member to gather epidermal tissue together.

2. The device for closing the tissue opening of claim 1, wherein the central angle is less than about 180° and greater than about 60°.

3. The device for closing the tissue opening of claim 1, wherein the central angle is less than about 150° and greater than about 90°.

4. The device for closing the tissue opening of claim 1, wherein the compression support frame comprises a body having an adhesive configured to be adhered on a tissue contact side of the body.

5. The device for closing the tissue opening of claim 1, wherein the compression support comprises an opening to accommodate the tension member.

6. The device for closing the tissue opening of claim 1, wherein the compression support comprises an opening to accommodate the tension member and a pawl to releasably engage complementary structures on the tension member.

7. The device for closing the tissue opening of claim 6, wherein the complementary structures comprise teeth formed in the tension member.

8. A device for closing the tissue opening of claim 1, wherein a bottom of the compression support frame has at least one convex surface.

9. A device for closing the tissue opening of claim 8, wherein a top of the compression support frame has a planar surface.

10. A device for closing the tissue opening of claim 1, wherein a top of the compression support frame has at least one convex surface.

11. A device for closing a tissue opening, the device comprising:

a compression support frame configured to contact tissue surrounding the tissue opening, the compression support frame comprising an arc-shape with a first linear edge, a second linear edge, an inner peripheral edge extending between the first linear edge and the second linear edge, and an outer peripheral edge extending between the first linear edge and the second linear edge, forming part of a circle having a dimension D1 from a center of the circle to the outer peripheral edge, and forming an arc whose central angle is less than 180° and greater than 45° and whose dimension D1 is constant over the outer peripheral edge, the compression support frame having a top surface disposed in a first plane, a bottom of the compression support frame comprises a plurality of elongate protrusions that extend parallel to the dimension D1 of the compression support frame and extend from the inner peripheral edge to the outer peripheral edge, each of the plurality of elongate protrusions comprising a long axis and a short axis and each of the plurality of elongate protrusions being orientated with the long axis extending parallel to the dimension D1;

a plurality of compression supports mounted to and extending from the top surface of the compression support frame, each compression support being rotatably mounted to an elongated protrusion extending from the top surface of the compression support frame, an axis of rotation of the elongated protrusion being perpendicular to the first plane of the compression support frame; and a plurality of tension members, each tension member being selectively slidable in relation to at least two compression supports of the plurality of compression supports to rotate the at least two compression supports about the compression support frame, wherein the at least two compression supports are configured to rotate based on a tension force applied by the tension member, the arc-shape of the compression support frame evenly distributing the tension force applied by the plurality of tension members to gather epidermal tissue together.

12. The device for closing the tissue opening of claim 11, wherein the central angle is less than about 180° and greater than about 60°.

13. The device for closing the tissue opening of claim 11, wherein the central angle is less than about 150° and greater than about 90°.

14. The device for closing the tissue opening of claim 11, wherein the compression support frame comprises a body having an adhesive configured to adhere on a tissue contact side of the body.

15. The device for closing the tissue opening of claim 11, wherein each of the plurality of compression supports comprises an opening to accommodate one tension member of the plurality of tension members and a pawl to releasably engage complementary structures on the one tension member of the plurality of tension members.

16. The device for closing the tissue opening of claim 15, where the complementary structures on the one tension member comprise teeth formed in the tension member.

* * * * *